(12) United States Patent
Welchel et al.

(10) Patent No.: US 7,475,982 B2
(45) Date of Patent: Jan. 13, 2009

(54) VAPOR BARRIER ATTACHMENT FOR EYEWEAR

(75) Inventors: Debra Welchel, Woodstock, GA (US); Raymond Cyr, Laval (CA); Luc Blanchette, Montreal (CA)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 206 days.

(21) Appl. No.: 11/639,940

(22) Filed: Dec. 15, 2006

(65) Prior Publication Data

US 2008/0143953 A1    Jun. 19, 2008

(51) Int. Cl.
G02C 11/08 (2006.01)
(52) U.S. Cl. .......................................... 351/62; 351/158
(58) Field of Classification Search ................... 351/41, 351/62, 124, 126, 158; 2/437–439
See application file for complete search history.

(56) References Cited

U.S. PATENT DOCUMENTS

| | | | |
|---|---|---|---|
| 4,419,993 A * | 12/1983 | Petersen | 128/201.15 |
| 4,799,782 A | 1/1989 | Tuttle | |
| 4,863,257 A | 9/1989 | Morgan | |
| 4,868,929 A | 9/1989 | Curcio | |
| 5,162,823 A | 11/1992 | Goldstein | |
| 5,319,397 A | 6/1994 | Ryden | |
| 5,351,339 A | 10/1994 | Reuber et al. | |
| 5,363,153 A | 11/1994 | Bailiff | |
| 5,459,533 A | 10/1995 | McCooeye et al. | |
| 5,584,078 A | 12/1996 | Saboory | |
| 5,610,669 A | 3/1997 | Kuipers et al. | |
| 5,652,637 A | 7/1997 | Marini | |
| 5,720,281 A | 2/1998 | Allen et al. | |
| 5,898,468 A | 4/1999 | Mage | |
| 5,907,385 A | 5/1999 | Flores et al. | |
| 5,956,119 A | 9/1999 | Gibbs | |
| 6,094,751 A | 8/2000 | Parks | |
| 6,318,369 B1 | 11/2001 | Gregory | |
| 6,783,235 B1 | 8/2004 | Lin | |
| 6,959,988 B1 | 11/2005 | Sheldon | |
| 7,077,137 B2 | 7/2006 | Russell | |
| 2004/0069302 A1 | 4/2004 | Wilson et al. | |

(Continued)

FOREIGN PATENT DOCUMENTS

WO    9704837    2/1997

OTHER PUBLICATIONS

Co-pending U.S. Appl. No. 11/413,575, filed Apr. 28, 2006.

(Continued)

*Primary Examiner*—Huy K Mai
(74) *Attorney, Agent, or Firm*—Dority & Manning, P.A.

(57) ABSTRACT

A combination includes eyewear, such as glasses, with a removable vapor barrier attachment. The eyewear includes a frame and lenses configured for protecting a user's eyes. The vapor barrier attachment is removably attached to the eyewear, and includes a base member removably attachable to the eyewear frame, and flap members extending from the base member. The flap members have a shape and length so as to extend longitudinally below the eyewear lenses. The flap members are attached to the eyewear along at least a portion of the length of the flap members and have a resilient sealing edge that conforms against the wearer's face to inhibit exhaled air from passing between the lenses and the wearer's face.

26 Claims, 5 Drawing Sheets

U.S. PATENT DOCUMENTS

2004/0107483 A1 6/2004 Thorson
2004/0125334 A1 7/2004 Olney
2005/0012893 A1 1/2005 Yamamoto
2005/0237477 A1 10/2005 Lindahl

OTHER PUBLICATIONS

Co-pending U.S. Appl. No. 11/413,576, filed Apr. 28, 2006.
Co-pending U.S. Appl. No. 11/413,521, filed Apr. 28, 2006.
Co-pending U.S. Appl. No. 11/413,517, filed Apr. 28, 2006.

* cited by examiner

VAPOR BARRIER ATTACHMENT FOR EYEWEAR

FIELD OF THE INVENTION

The present invention relates generally to the field of eyewear, and especially eyewear used for safety or recreational activities.

BACKGROUND

Eyewear for safety applications in industrial or medical use, or sports and other recreational activities, are used to protect a user's eyes. Such eyewear is usually designed to fit relatively closely to a user's face, so that noxious gas, liquid, particles, contaminants, and the like, do not touch or affect a user's eye(s).

Safety and some sports glasses or eyewear are often designed and formed such that they are bulky and heavy to wear. Some are tight-fitting and uncomfortable as well, such as goggles or masks. Further, such eyewear suffers from the lack of appropriate ventilation, resulting in moisture build-up and fogging of the lenses. This fogging may interfere with the user's vision as well as comfort, and can actually discourage the use of the eyewear. Moreover, eyewear that does not dissipate moisture may actually make it more difficult for a user to see when wearing the eyewear as compared to not wearing the eyewear.

Various attempts have been made in the art to reduce moisture buildup and fogging of eyewear. For example, it is know to treat eyewear lenses with a surfactant or other chemical composition to inhibit moisture build-up. However, such treatments are temporary and often require subsequent repeated applications. Skiers and other recreational users often carry a cloth impregnated with an anti-fogging composition to re-treat goggles or glasses as needed. This solution is inconvenient and not desirable in all instances. In the industrial and medical arts, the use of facemasks tends to direct warm, moist exhaled air towards the user's eyes. If the user wears glasses or a face shield, fogging is a problem. Various styles of facemasks incorporate a strip of foam or similar material across the top edge of the facemask to act as a gasket against the wearer's face in an attempt to minimize the fogging problem. This strip, however, tends to limit ventilation and escape of the exhaled air, which can increase the discomfort experienced by the user.

Therefore, alternative means for reducing moisture buildup and fogging with the use of safety and/or sports eyewear are still needed. The present invention relates to just such a solution.

SUMMARY

Objects and advantages of the invention will be set forth in part in the following description, or may be obvious from the description, or may be learned through practice of the invention.

As used herein, the term "eyewear" refers to eyeglasses, goggles, or other devises with protective lenses worn over the eyes.

A combination of eyewear with a removable vapor barrier attachment is proposed. The eyewear includes a frame and lenses configured for protecting the user's eyes. The type or style of eyewear is not a limiting factor. For example, the eyewear may be glasses or goggles with a frame and separate lenses, or a single lens that extends over both eyes. The eyewear may include a frame that surrounds the lenses, or the lenses may be exposed along the bottom edge thereof. The eyewear has particular usefulness in the industrial safety arts (e.g., industrial/manufacturing safety eyewear), but is also intended for other applications, such as recreational activity, medical applications, and so forth.

A vapor barrier attachment is removably affixed to the eyewear. This attachment device includes a base member that is removably attachable to the eyewear frame, and flap members that extend from the base member. The flap members have a shape and length so as to extend longitudinally below the lenses, and may be further attached to the lenses or to a portion of the eyewear frame that extends along the bottom edge of the lenses. The flaps members are made of a resilient material and have a profile that defines a resilient sealing edge that conforms against the wearer's face to inhibit exhaled air from passing between the lenses and the wearer's face. The sealing edge may be defined by a tapered edge of the flap members or other suitable profile.

The base member may include a releasable securing device that releasably secures the vapor barrier attachment to the eyewear frame. This securing device allows the wearer to quickly and easily attach and remove the vapor barrier device without tools or reconfiguring of the eyewear. This securing device may be a mechanical device, such as a clip that engages directly with the eyewear frame. In other embodiments, the securing device may include a releasable adhesive, hook-and-loop material, and so forth. In a particular embodiment, the securing device may include a magnetic coupling with the eyewear frame. For example, the base member may have a magnet embedded therein that attaches to a metal component of the eyewear frame.

The base member may include nose guard members of various shape and configuration. For example, the nose guard members may engage against a nose bridge portion or pads of the eyewear frame to further secure the vapor barrier attachment to the frame. The nose guard members may be configured so as not to contact the wearer's nose, or may be designed with a shape and configuration so as to engage the wearer's nose and move the eyewear frame away from the wearer's face. This configuration may be desired to increase ventilation between the lenses and the wearer's face.

In a particular embodiment of the eyewear, the lenses are exposed along a bottom edge thereof. In other words, the eyewear frame does not extend along the bottom edge of the lenses. With this embodiment, the flap members may be removably attachable directly to the lenses along the bottom edge of the lenses. For example, the flap members may include a groove defined along an upper portion thereof, with the bottom edge of the lenses insertable into the grooves.

In an alternate embodiment, the eyewear frame extends along a bottom edge of the lenses and the flap members are engaged directly against the frame adjacent to the bottom edge of the lenses. For example, the flap members may include a releasable attachment device, such as a mechanical device, a releasable adhesive, and the like, that attaches to the frame adjacent the bottom edge of the lenses. The flap members may include a gasket material that seals against the frame adjacent the bottom edge of the lenses.

The vapor barrier attachment may be formed from multiple pieces that are joined together, or may be formed from a unitary piece of resilient material, such as a synthetic or natural rubber-like or other resilient material. The flap members may have a preformed bias such that the sealing edges of the flap member are urged against the wearer's face. Such a bias may also aid with engagement of the flap members against the eyewear frame or lenses.

The combination may also include any manner of conventional facemask that is configured to fit over the wearer's nose and mouth. Such masks are commonly used as respiratory devices in industry, and are typically relatively rigid, molded cup-shaped masks. In the medical arts, typical facemasks are pleated flat panel masks, and are well known to those skilled in the art. The facemask may include a sealing material, such as an adhesive strip, along an upper edge thereof that releasably seals against an outer surface of the vapor barrier attachment.

The invention also includes the vapor barrier attachment as a stand-alone product for configuration with any manner of eyewear.

Aspects of the invention will be described in greater detail below by reference to particular embodiments illustrated in the drawings.

DETAILED DESCRIPTION

Figure 1:
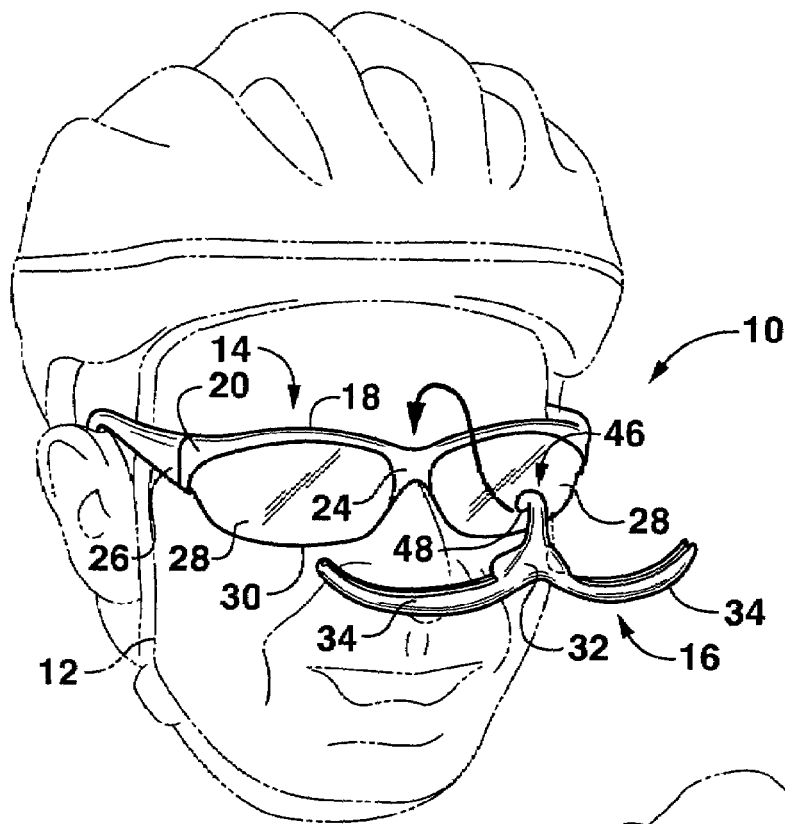
FIG. 1 is a perspective view of an embodiment of an eyewear and vapor barrier attachment combination according to the invention.

Reference will now be made in detail to embodiments of the invention, one or more examples of which are illustrated in the drawings. Each example is provided by way of explanation of the invention, and not meant as a limitation of the invention. For example, features illustrated or described as part of one embodiment, may be used with another embodiment, to yield still a further embodiment. It is intended that the present invention include modifications and variations to the embodiments described herein.

Figure 2:
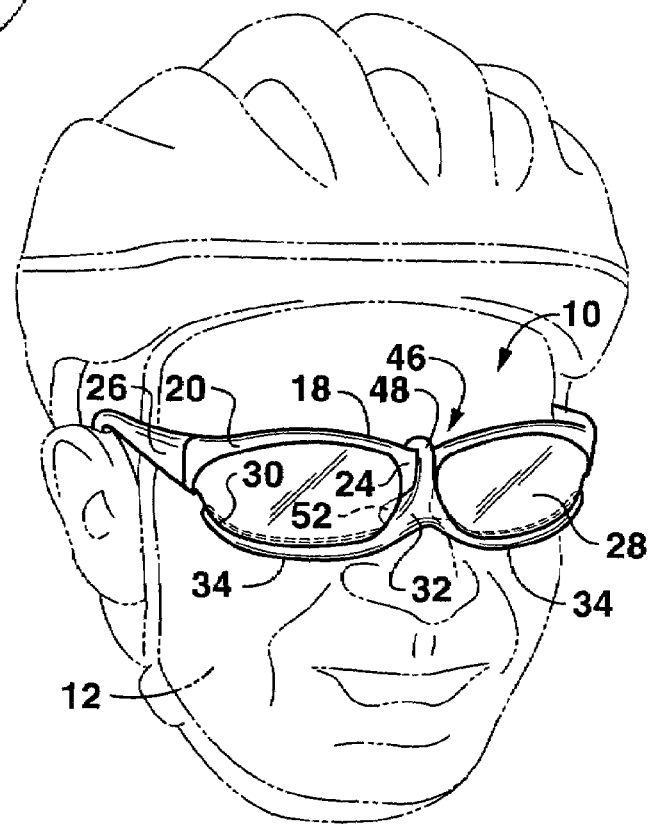
FIG. 2 is a perspective view of the combination of FIG. 1 with the vapor barrier device attachment configured on the eyewear.

FIGS. 1 and 2 illustrate an embodiment of a combination 10 that includes eyewear 14 and a vapor barrier attachment 16. In this particular embodiment, the combination 10 is worn by a user 12 in a recreational activity. The eyewear 14 includes a frame 18 having an upper portion 20 disposed along an upper edge of separate lenses 28. The lenses have a bottom edge 30. The eyewear frame includes a bridge portion 24 and earpieces 26. As discussed above, it should be appreciated that the eyewear 14 is not limited by any particular style, construction, or configuration. For example, the eyewear 14 depicted in FIG. 1 illustrates separate lenses 28. A single lens that extends across the bridge 24 to cover both of the user's eyes is also within the scope and spirit of the invention. Additionally, any manner or style of eyewear frame is contemplated within the invention.

The vapor barrier attachment 16 is removably attached to the eyewear 14 and includes a base member 32 that attaches to the eyewear frame 18, for example to the bridge member 24. In this regard, the vapor attachment 16 includes a securing device 46 that easily and quickly secures the vapor barrier attachment 16 to the eyewear frame 18. Various types of releasable securing devices may be used for this purpose. In the illustrated embodiment, the securing device 46 comprises a clip 48 that may be formed in the shape of a hook or other engaging structure. The clip 48 secures over the bridge portion 24 of the eyewear 14, as particularly illustrated in FIG. 2. Any manner of securing device may be utilized for this purpose, such as a releasable adhesive, hook-and-loop material, and so forth. The securing device 46 should be configured to readily attach to the eyewear frame 18 without extensive effort by the user 12, and without effecting the comfort or utility of the eyewear 14.

The vapor barrier attachment 16 also includes flap members 34 extending from a central base member 32. The flap members 34 have a shape and longitudinal length so as to extend longitudinally along the lower edge 30 of the lenses 28. The flap members 34 are made of a resilient material and have a profile that defines a resilient sealing edge 38 (FIG. 3) along the bottom portion of the flap members 34. The resilient material may be, for example, any manner of natural or synthetic rubber or rubber-like material that allows the flap members 34 to form the sealing edge 36 and conform to the user's face along the bottom of the lenses 28. Referring to FIG. 4B, for example, the flap members 34 may have a relatively rigid upper portion 36 with a tapering profile to the sealing edge 38. The upper portion 36 may have a preformed shape and bias that urges the flap members 34, and particularly the sealing edge 38, against the wearer's face and the eyewear 14. When the vapor barrier attachment 16 is donned as illustrated in FIG. 2, the flap members 34 define an effective seal against the wearer's face below the lenses 28 so that exhaled moist air from the user is prevented from passing under the lenses, which could result in undesirable fogging of the lenses.

Figure 3:
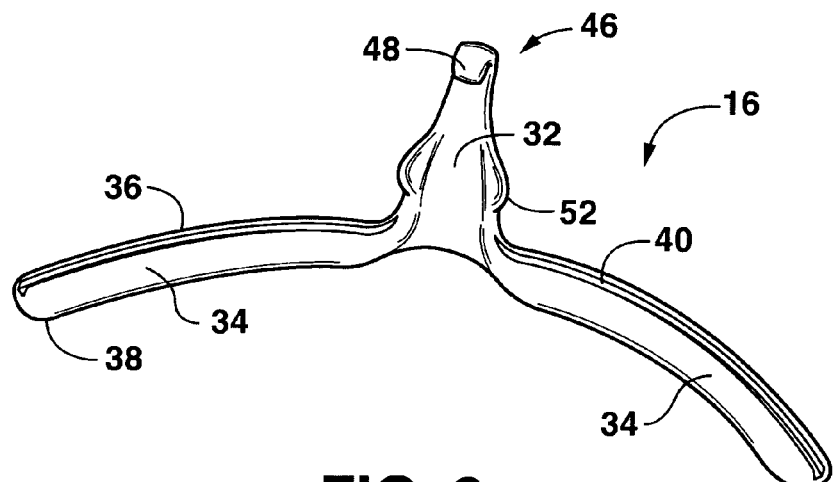
FIG. 3 is a back perspective view of an embodiment of a vapor barrier attachment according to the invention.

FIG. 3 illustrates the back of an embodiment of the vapor barrier attachment 16. This particular embodiment includes a groove 40 defined along the upper portion 36 of each flap member 34. This groove is configured for receipt of the exposed bottom edge 30 of the lenses depicted in the eyewear 14 of FIG. 1. FIG. 2 illustrates the bottom edge 30 of the lenses engaged within the groove 40 when the vapor barrier attachment 16 is properly attached to the eyewear. This groove serves to secure the flap members 34 in position relative to the lenses 28 so that the sealing edge 38 of the flap members 34 are maintained in a biased state against the user's face.

Figure 7:
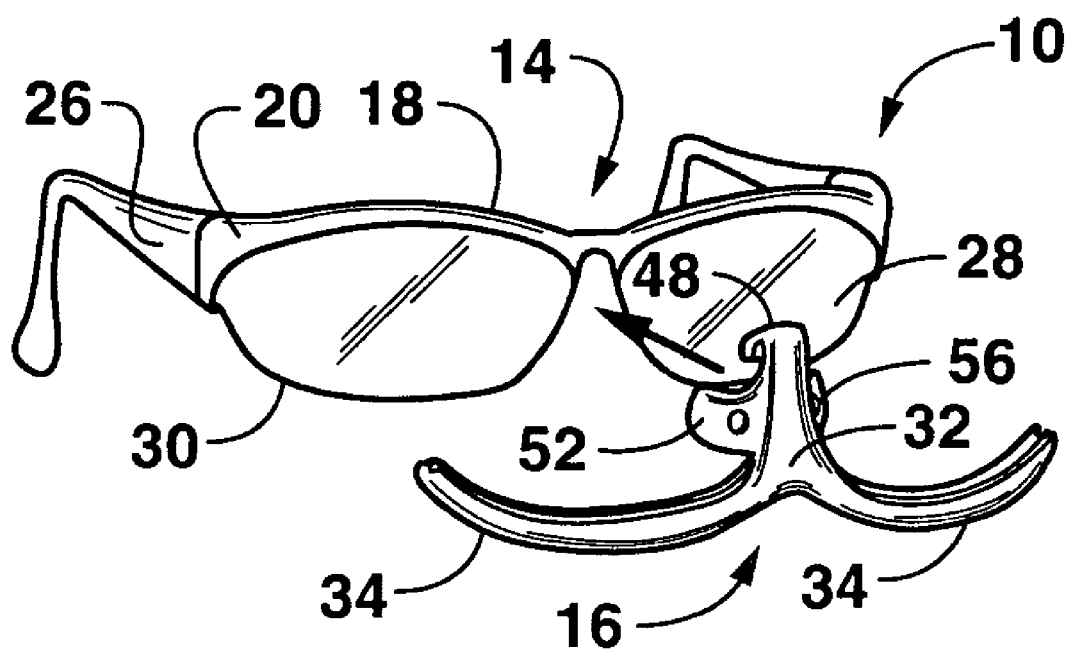
FIG. 7 is a perspective view of still another embodiment of an eyewear and vapor barrier attachment combination according to the invention.

Still referring to FIG. 3, the base member 32 may include nose guard members 52 extending therefrom. The nose guard members 52 may have any suitable design or shape depending on their desired function. For example, the nose guard members 52 may be provided as an additional means for attaching the vapor barrier attachment 16 to the eyewear 14. For example, referring to FIG. 4B, the nose guard members 52 may include protrusions 56 or other suitable structure that engage against or below the portion of the eyewear frame 18 defining the bridge portion 24. The nose guard members 52 may be designed so as not to contact the wearer's face or nose, but to function primarily as an additional securing mechanism for the vapor barrier attachment 16. In an alternate embodiment, the nose guard members 52 may be designed to contact the wearer's face across the nose in addition to the nosepieces provided with the eyewear 14. In still another embodiment illustrated particularly in FIG. 7, the nose guard members 52 may be designed with a sufficient length and configuration so as to contact the wearer's nose and displace the function of the eyewear nosepieces. The nose guard members 52 may have a length so as to move the eyewear frame 18 away from the wearer's face as compared to the nose pads provided with the eyewear 14. By moving the eyewear away from the wearer's face, ventilation may be improved between the lenses and the wearer's face.

Figure 4A:
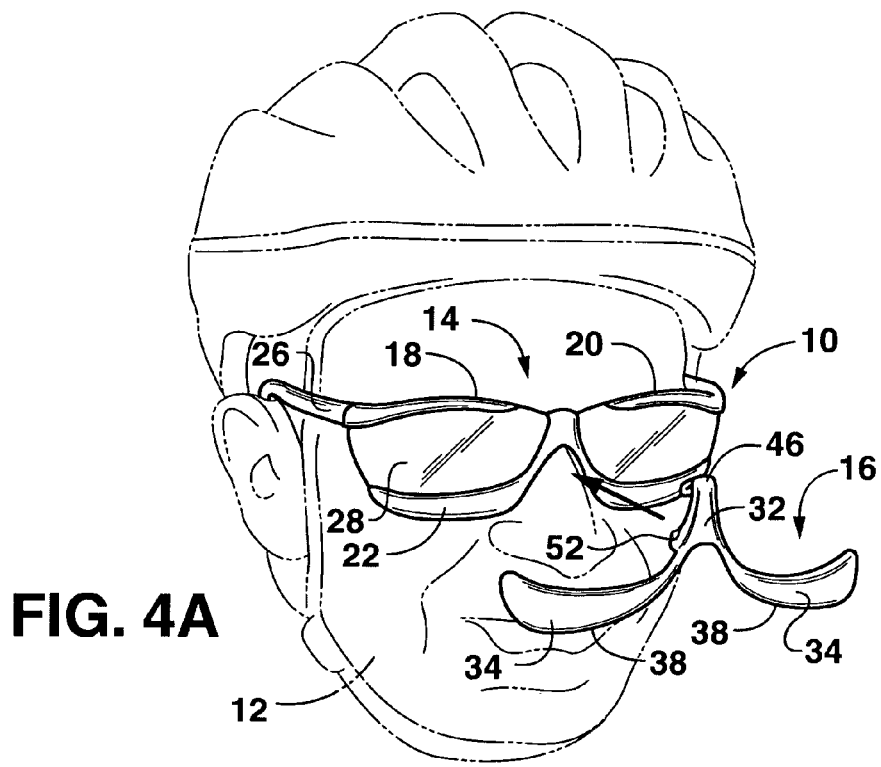
FIG. 4A is a perspective view of an alternative embodiment of an eyewear and vapor barrier attachment combination according to the invention.
Figure 4B:
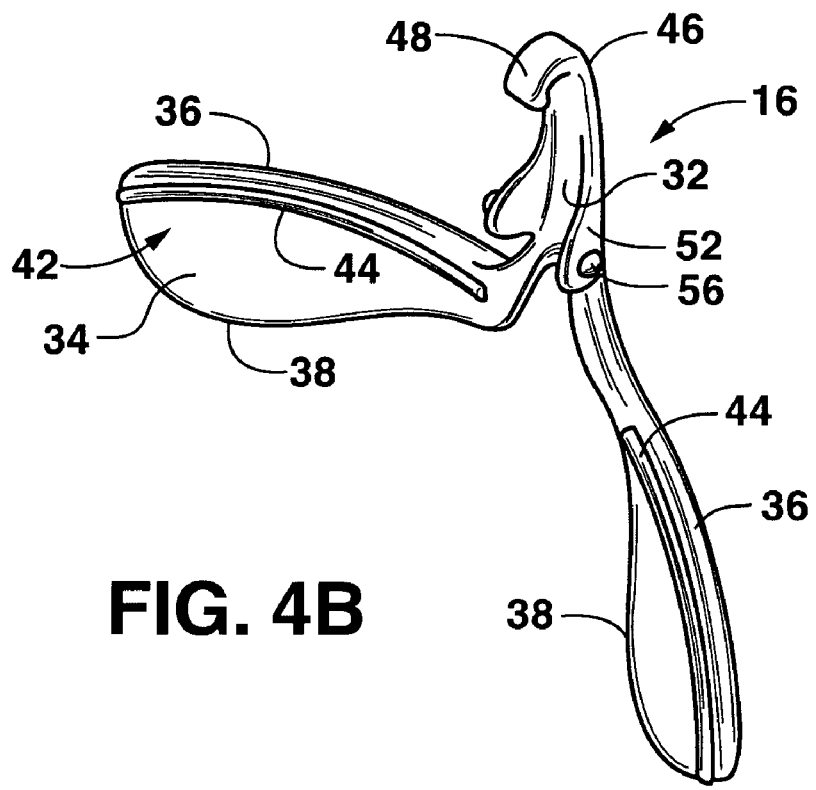
FIG. 4B is a back perspective view of the vapor barrier attachment of FIG. 4A.

In the embodiment illustrated in FIG. 4A, the eyewear 14 includes a lower frame portion 22 disposed along the bottom of the lenses 18. The vapor barrier attachment 16 is particularly configured to releasably attach with this particular style of eyewear 14. For example, referring to FIG. 4B, the flap members 34 may include an attaching device 42 disposed along the upper portion 36 for directly securing the flap members 34 along the lower frame portions 22. This additional attachment device 42 may include, for example, any manner of releasable adhesive, hook-and-loop material, mechanical device, and so forth. In the illustrated embodiment, the attachment device 42 includes a longitudinally extending strip 44 of adhesive foam material. This material 44 also acts as an additional gasket or seal between the flap members 34 and the lower frame portions 22 of the eyewear 14.

In the illustrated embodiments, the vapor barrier attachment 16 is formed as a unitary piece from any suitable resilient material. It should be appreciated that the vapor barrier attachment 16 may be formed from multiple pieces. For example, the base member 32 may be formed from a molded plastic component while the flap members 34 are formed from a relatively soft rubber-like material that is attached to the base member 32.

Figure 5A:
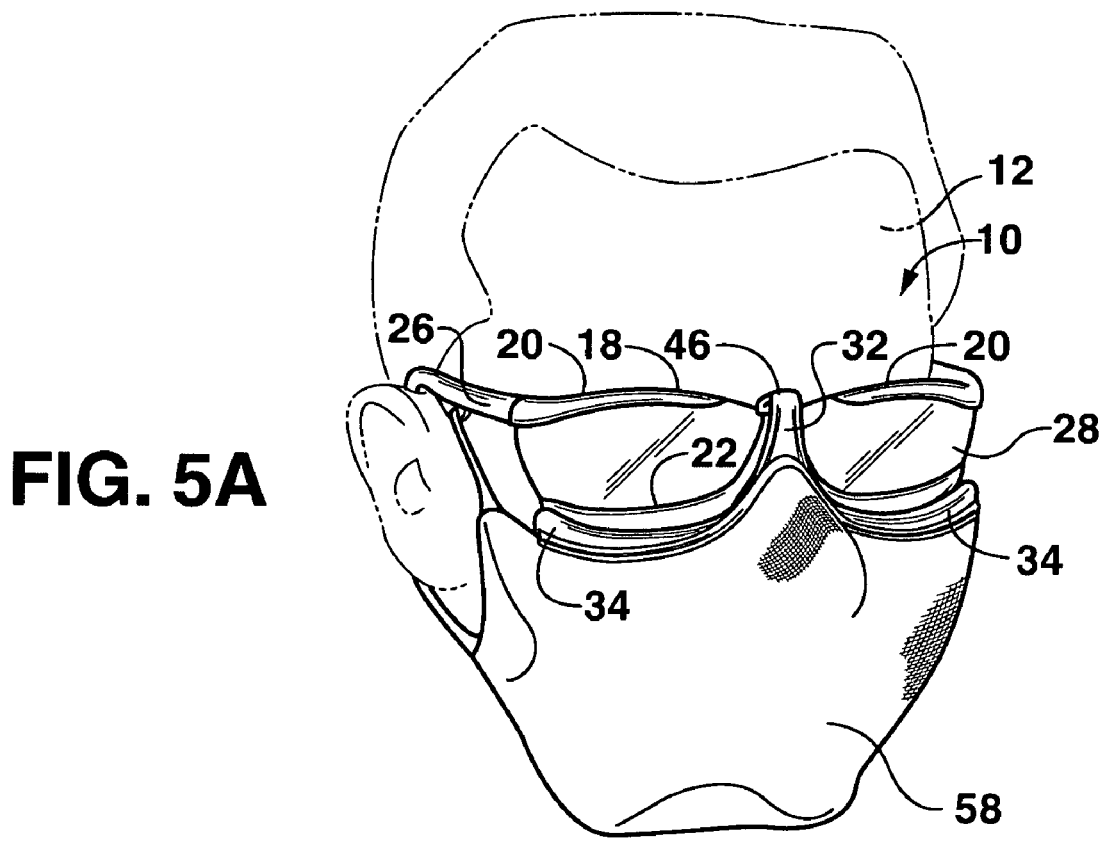
FIGS. 5A and 5B are perspective views of another embodiment of an eyewear and vapor barrier attachment according to the invention that also incorporates a facemask.
Figure 5B:
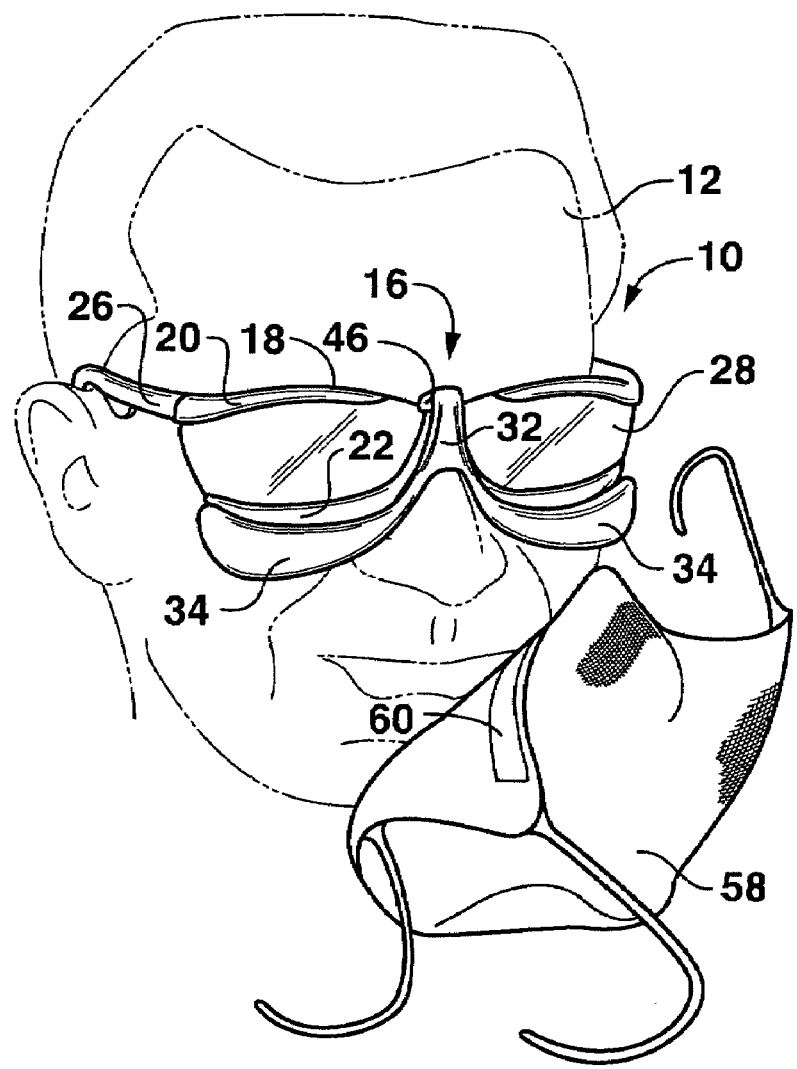

FIGS. 5A and 5B illustrate an embodiment wherein the combination 10 includes any manner of conventional facemask 58. The type of mask depicted in the figure is for illustration purposes only, and it should be appreciated that the mask configuration and intended purpose are not limiting factors. The particular combination 10 may be useful in the industrial safety arts as a respiratory aid, or the medical or healthcare arts. The facemask 58 may be a molded mask or a flat panel style mask, and may be combined with any manner of combination of eyewear 14 and vapor barrier attachment 16. In the illustrated embodiment, the vapor barrier 16 is configured with eyewear 14 having a lower frame portion 22, as discussed above. The facemask 58 may include an attachment mechanism along the upper edge thereof that releasably attaches to the outer surface of the flap members 34. For example, referring to FIG. 5B, a strip 60 of releasable adhesive may be provided along the top edge of the facemask 58 for releasably attaching to the flap members 34. This particular configuration may further reduce undesirable fogging of the eyewear lenses 28 that may result from moist exhaled air being otherwise directed between the mask 58 and the flap members 34 onto the outside surface of the lenses 28.

Figure 6:
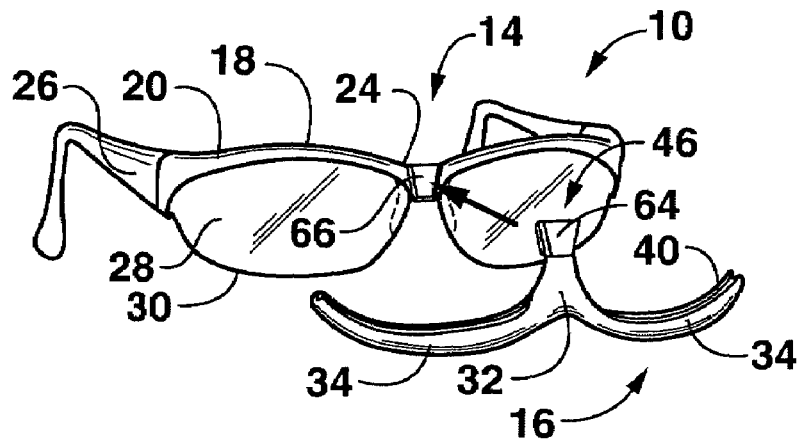
FIG. 6 is a perspective view of an alternative embodiment of an eyewear and vapor barrier attachment combination according to the invention.

FIG. 6 illustrates an embodiment of a combination 10 of eyewear 14 and vapor barrier attachment 16 wherein the securing device 46 between the attachment 16 and eyewear 14 includes a magnetic coupling between the components. For example, a magnet 64 may be embedded or otherwise attached to the base member 32 of the vapor barrier attachment 16. This magnet 64 may couple to any metal component 66 disposed on the nose portion 24 of the eyewear frame 18. Conversely, the magnet 64 may be provided on the eyewear 14, with the metal component 66 being disposed on the vapor barrier attachment 16.

It should be appreciated by those skilled in the art that various modifications and variations may be made to features of the dispenser described herein, particularly to the mechanical and control circuitry aspects of the dispenser, without departing from the scope and spirit of the invention. It is intended that the invention include all such variations.

What is claimed is:

1. A combination of eyewear with a removable vapor barrier attachment, comprising:
    eyewear comprising a frame and lenses configured for protecting a user's eyes;
    a vapor barrier attachment removably configured on said eyewear, said vapor barrier attachment comprising a base member removably attachable to said eyewear frame, and flap members extending from said base member, said flap members having a shape and length so as to extend longitudinally below said lenses;
    said flap members attached to said eyewear along at least a portion of the length of said flap members and comprising a resilient sealing edge that conforms against the wearer's face to inhibit exhaled air from passing between said lenses and the wearer's face.

2. The combination of claim 1, wherein said base member comprising a releasable securing device that releasably secures said attachment device to said eyewear frame.

3. The combination of claim 2, wherein said securing device comprises a clip.

4. The combination of claim 2, wherein said securing device comprises a magnetic coupling.

5. The combination of claim 1, wherein said base member comprises nose guard members that engage against a nose bridge portion of said eyewear frame.

6. The combination of claim 5, wherein said nose guard members have an extension length so as to engage the wearer's nose and move said eyewear frame away from the wearer's face.

7. The combination of claim 1, wherein said lenses are exposed along a bottom edge thereof, said flap members removably attachable directly to said lenses along said bottom edge.

8. The combination of claim 7, wherein said flap members comprise a groove defined along an upper portion thereof, said bottom edge of said lenses insertable into said grooves.

9. The combination of claim 1, wherein said frame extends along a bottom edge of said lenses, said flap members engaged directly against said frame adjacent said bottom edge of said lenses.

10. The combination of claim 9, wherein said flap members comprise a releasable attachment device that attaches to said frame adjacent said bottom edge of said lenses.

11. The combination of claim 9, wherein said flap members comprise a gasket material that seals against said frame adjacent said bottom edge of said lenses.

12. The combination of claim 1, further comprising a facemask configured to fit over the wearer's nose and mouth, said facemask comprising a sealing material along an upper edge thereof that releasably seals against said vapor barrier attachment.

13. The combination of claim 12, wherein said sealing material comprises an adhesive strip.

14. The combination of claim 1, wherein said vapor barrier attachment is formed from a unitary piece of resilient material, said flap members having a preformed bias such that said sealing edges are urged against the wearer's face.

15. A vapor barrier attachment for removable securement to eyewear, the eyewear having a frame and lenses configured to protect a wearer's eyes, said attachment comprising:

a base member removably attachable to the eyewear frame, and flap members extending from said base member, said flap members having a shape and length so as to extend longitudinally below the eyewear lenses;

said flap members attachable to the eyewear along at least a portion of the length of said flap members and comprising a resilient sealing edge that conforms against the wearer's face to inhibit exhaled air from passing between the lenses and the wearer's face.

16. The vapor barrier attachment of claim 15, wherein said base member comprising a releasable securing device that releasably secures said attachment to the eyewear frame.

17. The vapor barrier attachment of claim 16, wherein said securing device comprises a clip.

18. The vapor barrier attachment of claim 16, wherein said securing device comprises a magnetic coupling.

19. The vapor barrier attachment of claim 15, wherein said base member comprises nose guard members configured to engage against a nose bridge portion of the eyewear frame.

20. The vapor barrier attachment of claim 19, wherein said nose guard members have an extension length so as to engage the wearer's nose and move the eyewear frame away from the wearer's face.

21. The vapor barrier attachment of claim 15, wherein said flap members are removably attachable directly to exposed bottom edges of the eyewear lenses.

22. The vapor barrier attachment of claim 21, wherein said flap members comprise a groove defined along an upper portion thereof, said groove configured for receipt of the bottom edge of the eyewear lenses therein.

23. The vapor barrier attachment of claim 15, wherein said flap members engage directly against a portion of the eyewear frame adjacent bottom edges of the eyewear lenses.

24. The vapor barrier attachment of claim 23, wherein said flap members comprise a releasable attachment device that attaches to the eyewear frame adjacent the bottom edge of the lenses.

25. The vapor barrier attachment of claim 23, wherein said flap members comprise a gasket material that seals against the eyewear frame adjacent the bottom edge of the lenses.

26. The vapor barrier attachment of claim 15, wherein said vapor barrier attachment device is formed from a unitary piece of resilient material, said flap members having a preformed bias such that said sealing edges are urged against the wearer's face.

* * * * *